United States Patent [19]

Simon et al.

[11] Patent Number: 5,047,434
[45] Date of Patent: Sep. 10, 1991

[54] METHOD FOR WEIGHT GAIN-INCREASING OF FODDER UTILIZATION OF PIGS, CATTLE OR POULTRY

[75] Inventors: Ferenc Simon; Károly Magyar; Attila Nagy; Lajos Fekete; László Puskás; Pál Fekete; István Simonyi; János Egri; Katalin Zukovics née Sümeg, all of Budapest, Hungary

[73] Assignee: Egis Gyogyszergyar, Budapest, Hungary

[21] Appl. No.: 375,507

[22] Filed: Jul. 5, 1989

[30] Foreign Application Priority Data

Jul. 5, 1988 [HU] Hungary .................. 3487/88

[51] Int. Cl.⁵ .......................................... A61K 31/135
[52] U.S. Cl. ............................................... 514/653
[58] Field of Search ....................................... 514/653

[56] References Cited

U.S. PATENT DOCUMENTS

| 3,818,101 | 6/1974 | Baile et al. | 514/653 |
| 3,937,838 | 2/1976 | Wetterlin et al. | 514/653 |
| 4,407,819 | 10/1983 | Kiernan et al. | 514/653 |
| 4,649,158 | 3/1987 | Asato et al. | 514/653 |
| 4,761,421 | 8/1988 | Muir | 514/653 |

Primary Examiner—Stanley J. Friedman
Assistant Examiner—Kevin Weddington
Attorney, Agent, or Firm—Keil & Weinkauf

[57] ABSTRACT

The invention relates to weight gain-increasing compositions, particularly fodder supplement, premix, drinking water supplement, bolus and/or microcapsule containing 0.001 to 90% by weight of 1-(3,5-dihydroxyphenyl)-2-(tertiary butylamino)-ethanol or a physiologically acceptable acid addition salt thereof as active ingredient in admixture with inert solid and/or liquid carrier(s).

4 Claims, No Drawings

METHOD FOR WEIGHT GAIN-INCREASING OF FODDER UTILIZATION OF PIGS, CATTLE OR POULTRY

This invention relates to a weight gain-increasing composition, particularly to a fodder supplement, premix, drinking water supplement, bolus and/or microcapsule. According to an other aspect of the invention, there is provided a process for the preparation of a weight gain-increasing fodder from the above fodder supplement or premix, respectively.

In keeping of animals, the economy of flesh production is significantly influenced by the extent of utilization of the fodder used for feeding the animals, i.e. the amount of fodder required to achieve a weight gain of 1 kg. Another important parameter is the period during which the animals reach the slaughter weight. Obviously, the lower is the fodder amount required and the shorter is the time of feeding necessitated to achieve the slaughter weight, the more economical is the flesh production.

The economy of flesh production is influenced also by the composition of the fodder used for feeding the animals (chiefly cattle, swine, sheep and poultry). Therefore, fodders with a high protein content are used which also contain various vitamins and trace elements. However, these biological valuable fodders are rather expensive.

In the last decades, the economy of flesh production has been enhanced also by adding to the fodder a gain-increasing additive which promotes fodder utilization.

Such a gain-increasing agent, used for ruminants, is monensin, chemically 4-{2-[2-ethyl-3'-methyl-5'-(tetrahydro-6-hydroxy-6-hydroxymethyl-3,5-dimethyl-2-pyranyl)-perhydro-2,2'-difuran-5-yl]-9-hydroxy-2,8-dimethyl-1,6-dioxaspiro[4.5]dec-7-yl}-3-methoxy-2-methylvaleric acid. Though monensin is useful to increase the gain, it has the drawback that it results in a fatty meat [Veterinary Pharmacology and Therapeutics, 5th Edition 1982, Iowa State University Press, USA, pp. 877, 1050 to 1057 and 1101].

In pig fattening, carbadox [chemically 3-methyl-(quinoxalin-2-yl-methylene)-carbazate-$N^1$, $N^4$-dioxide] is used. The most important disadvantage of carbadox is that it is eliminated from the organism of the swine within a very long time, thus it may not be administered during the last 70 days before slaughtering [Veterinary Pharmacology and Therapeutics, 4th Edition 1977, Iowa State University Press, pp. 962 and 1319; Shively et al.: J. Animal Sci. 27, 1136 (1968); Thrasher et al.: ibidem 27, 1137 (1968); Thrasher et al.: ibidem 28, 208 (1969)].

In keeping of poultry neomycin sulfate, an antibiotic, is used to increase weight gain. The drawbacks of it are that its gain-increasing effect is weak and a cross-resistance may be developed against other antibiotics [Hossoff: Handbook of Veterinary Drugs, Springer Publishing Co., New York, 1974, p. 368)].

The aim of the present invention is to provide a weight gain-increasing composition making possible an economical flesh production, shifting the flesh/fat ratio in animals in favor of the flesh and thereby resulting in animals having flesh with a relatively low fat content upon reaching slaughter weight.

Now it has been found that the above aim can be achieved by a weight gain-increasing composition or fodder, respectively, containing 1-(3,5-dihydroxyphenyl)-2-(tertiary butylamino)-ethanol or a physiologically acceptable acid addition salt thereof as weight gain-increasing active ingredient.

1-(3,5-Dihydroxyphenyl)-2-(tertiary butylamino)-ethanol (generic name: terbutaline) is a known sympathomimetic agent used particularly as a bronchodilator in the human therapy (see U.S. Pat. No. 3,937,838). Up to the present, this compound has not been used either in veterinary medicine or in animal keeping.

The invention is based on the recognition that by feeding or treating, respectively, farm animals (such as swine, cattle, sheep or poultry) with a composition or fodder, respectively, containing terbutaline or a physiologically acceptable acid addition salt thereof, the time required to achieve the slaughter weight is significantly shortened and the amount of fodder consumed by the animals becomes lower since the rate of protein synthesis in the animal organism is enhanced whereby fat deposition is relatively decreased. Considering that terbutaline is chemically a substituted catecholamine is contrast to the known gain-increasing additives, it is not a foreign substance to the organism. Consequently, it is not necessary to deprive the animals of terbutaline before slaughtering and practically the elimination thereof should not be waited out.

The weight gain-increasing composition according to the invention is particularly a fodder supplement, premix, drinking water supplement, bolus and/or microcapsule containing terbutaline or a physiologically acceptable acid addition salt thereof in an amount of 0.001 to 90% by weight in admixture with inert solid and/or liquid carrier(s).

The term "physiologically acceptable acid addition salt of terbutaline" as used here means acid addition salts of terbutaline formed with physiologically acceptable inorganic or organic acids such as hydrochloric, sulfuric, acetic, fumaric, benzoic acid and the like. It is preferred to use the sulfate of terbutaline.

Terbutaline or its acid addition salt can be prepared by using e.g. the process described in the U.S. Pat. No. 3,937,838.

The term "fodder supplement", as used herein, means a composition which can be mixed to the animal fodder as an additive in a ratio ensuring a concentration of $10^{-5}$ to $10^{-2}\%$ by weight of the active ingredient in the fodder. The fodder supplement according to the invention contains terbutaline or a physiologically acceptable acid addition salt thereof in an amount of 0.001 to 25.0% by weight in admixture with the usual carrier(s) of fodder supplements.

The term "premix" means a composition which can be used as a fodder after dilution with the commonly used components of animal fodders. The premix according to the invention contains terbutaline or a physiologically acceptable acid addition salt thereof in an amount of 0.001 to 25.0% by weight in admixture with the usual carrier(s) of premixes.

As usual carriers of fodder supplements and premixes, materials of plant or animal origin can be used which are useful for feeding. It is suitable to use maize, wheat, barley, soy, fodder bean, rye and alfalfa in the form of grains, grits or meal as well as fish-meal, meat-meal and the like. In addition, starch of e.g. maize, wheat or potato as well as inorganic materials, e.g. silicon dioxide, calcium carbonate, dicalcium phosphate and the like, may be used as carrier(s). Antioxidants and wetting agents, e.g. a non-toxic oil, preferably soy, maize or mineral oil, or an alkylene glycol may also be present as carrier(s).

The premix according to the invention may contain also various vitamins, mineral salts and trace elements.

The fodder supplement and/or premix according to the invention is (are) prepared by mixing the components with each other and then, before the use, by mixing them with the usual components of animal fodders to obtain a fodder containing $10^{-5}$ to $10^{-2}\%$ by weight of terbutaline. E.g. the above-listed carriers may be used as the usual components of animal fodders.

The fodder supplement and/or premix according to the invention preferably contains the active ingredient in an amount of 0.02 to 0.3% by weight.

The term "drinking water supplement", as used herein, means a composition which is mixed with the drinking water of the animals as an additive in an amount ensuring a concentration of $10^{-5}$ to $10^{-2}\%$ by weight of the active ingredient in the drinking water. The drinking water supplement according to the invention contains terbutaline or a physiologically acceptable acid addition salt thereof in an amount of 0.001 to 90% by weight in admixture with the usual carrier(s) of the drinking water supplements. As carriers, substances promoting the dissolution or homogeneous distribution of the active ingredient in the drinking water such as pulverized glucose as well as surfactants, dispersing agents and the like are preferably used.

Particularly in poultry flesh production it is preferable to administer terbutaline or a physiologically acceptable acid addition salt thereof in the drinking water of the animals.

When feeding larger animals, it may be suitable to give terbutaline to the animals in bolus form. The bolus contains 0.001 to 80% by weight of terbutaline or a physiologically acceptable acid addition salt thereof in admixture with the usual carries of boluses. A bolus can conveniently be prepared by suspending the active ingredient in a melt of waxes such as bee wax, carnauba wax or the like, adjusting a density over 2.5 g/ml by adding barium sulfate, then pouring the suspension obtained into a casting mould and allowing it to cool.

Terbutaline also may be administered to the animals in the form of microcapsules. The microcapsules contain 0.001 to 90% by weight of terbutaline or a physiologically acceptable acid addition salt thereof in admixture with the usual carrier(s) of microcapsules. It is advantageous to use water-insoluble polymers as carriers.

Carriers and preparation methods which can be used in the compositions or in the preparation of the compositions according to the invention are described in the following handbooks: Remington's Pharmaceutical Sciences 16th Edition, Mack Publishing Co., Easton, USA, 1980; Formulation of Veterinary Dosage Form, Marcel Dekker Inc., New York - Basel, 1983.

According to the invention, the weight gain of farm animals, particularly of poultry, swine, cattle and/or sheep, is increased and the fodder utilization is improved by introducing an effective amount of the active ingredient of the composition according to the invention into the stomach or blood flow of the animal.

The effect of terbutaline on feeding animals was studied on 30 days old pigs weaned from the brood sow. The maximum genetical homogeneity of the groups consisting of 12 animals each was ensured by selecting the most developed pigs from each litter and putting one of them in each group. Thus, each pig had a full brother (sister) in the other groups and therefore, the groups were qualified to be of the same origin. At the beginning of the experiment, the average weight of the pigs in the groups varied between 9.56 and 9.61 kg and the latter group consisting of the individuals with the highest weight was used as control.

The animals were fed pig food with the following composition for 5 weeks:

| | |
|---|---|
| Maize | 625 g/kg |
| Extracted soy grits | 140 g/kg |
| Fish meal | 40 g/kg |
| Meagre milk powder | 150 g/kg |
| Sugar | 20 g/kg |
| A concentrate containing vitamins, amino acids and antioxidant (BCR-222) | 5 g/kg |
| Monocalcium phosphate | 7 g/kg |
| Fodder lime | 12 g/kg |
| Fodder salt | 1 g/kg |
| | 1000 g/kg |

The digestible protein content of the fodder amounted to 174.9 g/kg. To the above pig food, 5 ppm of terbutaline sulfate in group 1 and 50 ppm of carbadox, respectively, in group 2 were added. Group 3 served as control which received only the pig food. The results are summarized in Table 1.

TABLE 1

| | No. of the animal group | | |
|---|---|---|---|
| | 1 Terbutaline-treated | 2 Carbadox-treated | 3 Control |
| Weight before feeding | | | |
| Average, kg | 9.56 | 9.58 | 9.61 |
| Total, kg | 114.7 | 114.9 | 115.3 |
| Weight at the end of feeding | | | |
| Average, kg | 19.84 | 19.82 | 18.51 |
| Total, kg | 238.1 | 237.9 | 222.1 |
| Total weight gain, kg | 123.4 | 123.0 | 106.8 |
| Duration of feeding, day | 34 | 34 | 34 |
| Total food consumed, kg | 220 | 237 | 219.4 |
| Digestible rough protein in the food, kg | 38.47 | 41.45 | 38.37 |
| Food consumed for a weight gain of 1 kg, kg | 1.78 | 1.93 | 2.05 |
| Digestible rough protein consumed for a weight gain of 1 kg, kg | 0.311 | 0.337 | 0.358 |

It is obvious from Table 1 that the economy of flesh production was significantly increased on the effect of 5 ppm terbutaline being present in the food. The consumption of practically the same amount of food ensured a weight gain exceeding by 15.5% that of the control group. Thus, an essentially lower amount of food or protein, respectively, was required to achieve a weight gain of 1 kg in the terbutaline-treated group in comparison to the control group.

In case of carboadox, used as reference compound, a weight gain of about the same extent was observed as that on the terbutaline-treated animals but the fodder consumption was higher. Accordingly, the carbadox-treated animals consumed a higher amount of food or protein, respectively.

The invention is illustrated in detail by the following non limiting Examples.

EXAMPLE 1

30 g of terbutaline are homogenized with 99.97 kg of maize starch. Before use, the fodder supplement obtained is mixed to a 100- fold weight of fodder.

EXAMPLE 2

250 g of terbutaline sulfate are homogenized with 250 g of silicon dioxide, 500 g of extracted soy grits and 200 g of maize meal to give a premix containing 25% by weight of terbutaline sulfate, which is then diluted to its $10^5$-fold for preparing a fodder.

EXAMPLE 3

10 g of terbutaline sulfate are dissolved in 1 liter of propylene glycol. After dilution with water to e.g. 2000-fold of its weight, the solution obtained is used for the watering of poultry.

EXAMPLE 4

20 g of terbutaline sulfate (wherein 90% by weight of the particles are less than 10 μm in size), 160 g of calcium sulfate dihydrate (wherein 90% by weight of the particles are less than 10 μm in size) and 20 g of ethyl cellulose (with an ethoxy content of 48 to 49.5% by weight) dissolved in a 4:1 by weight mixture of toluene and ethanol in an amount to give a concentration of 5% by weight (viscosity 95 to 105 cP) are suspended in 1 liter of cyclohexanone and after heating under a reflux condenser at 80° C. for 1 hour, the suspension is cooled to room temperature under constant stirring. The microcapsules obtained are filtered and dried in the air to give microcapsules containing 10% by weight of terbutaline sulfate each. The microcapsules are mixed with a $10^4$ to $10^5$-fold weight of fodder before administration to the animals.

EXAMPLE 5

After suspending 80 g of terbutaline sulfate (wherein 90% by wight of the particles are less than 10 μm in size) in the melt of 200 g of spermaceti (a mixture of esters of fatty acids with cetyl alcohol) and 200 g of carnauba wax at 90° to 95° C., 320 g of barium sulfate are mixed to the suspension which is then filled into glass cylinders of 1.25 cm in diameter and 10 cm in length and left to cool down. The boluses solidified are extruded from the glass cylinders to obtain boluses each of which weights 80 g and contains 10% by wight of terbutaline sulfate. The boluses obtained may be used for the individual treatment of cattles.

What is claimed is:

1. A method for increasing the weight gain and improving the fodder utilization of pigs, cattle or poultry, which comprises: introducing into the stomach of the animal as the active agent a physiologically effective amount of 1-(3,5-dihydroxyphenyl)-2-(tertiary butylamino)-ethanol or a physiologically acceptable acid addition salt thereof.

2. The method of claim 1, wherein the active agent is introduced into pigs.

3. The method of claim 1, wherein the active agent is introduced into cattle.

4. The method of claim 1, wherein the active agent is introduced into poultry.

* * * * *